(12) United States Patent
Vittori

(10) Patent No.: US 6,482,942 B1
(45) Date of Patent: Nov. 19, 2002

(54) METHOD OF ISOLATING MUCILAGINOUS POLYSACCHARIDES AND USES THEREOF

(75) Inventor: Natale Vittori, Coppell, TX (US)

(73) Assignee: Biotechnology Services and Consulting, Inc., Coppell, TX (US)

( * ) Notice: Subject to any disclaimer, the term of this patent is extended or adjusted under 35 U.S.C. 154(b) by 0 days.

(21) Appl. No.: 09/481,111

(22) Filed: Jan. 11, 2000

Related U.S. Application Data

(60) Provisional application No. 60/115,619, filed on Jan. 12, 1999.

(51) Int. Cl.[7] .................................................. C07H 1/08
(52) U.S. Cl. ........................ 536/128; 536/127; 514/53; 514/54
(58) Field of Search ................................ 536/128, 127; 514/53, 54

(56) References Cited

U.S. PATENT DOCUMENTS

| | | | | |
|---|---|---|---|---|
| 4,051,314 A | * | 9/1977 | Ohtsuka et al. | 536/1 |
| 4,271,151 A | | 6/1981 | Hotta | |
| 4,673,530 A | * | 6/1987 | Hara | 252/398 |
| 4,764,507 A | | 8/1988 | Takeo | |
| 4,769,363 A | | 9/1988 | Misaki | |
| 4,957,907 A | | 9/1990 | McAnalley | |

FOREIGN PATENT DOCUMENTS

| | | |
|---|---|---|
| GB | 371811 | 4/1932 |
| GB | 1042379 | 9/1966 |

OTHER PUBLICATIONS

Westerlund, E. et al "Isolation and chemical characterization of water–soluble mixed–linked beta–glucans . . ." Carbohyd. Polymers, 1993, vol. 20, pp. 115–123.*

Gowda et al., 1979, Carbohydrate Research 72:201–205.
Jones, 1953, Biochimica. Biophys. Acta 10:607.
Kodym, 1991, Pharmazie 46:217–219, abstract only.
Manna and McAnalley, 1993, Carbohydrate Research 241:317–319.
Ozawa, 1987, Phytochemistry 26:2937–2942.
Scott, 1955, Chemistry and Industry.
'tHart et al., 1989, Planta Medica 55:509–512.
Talesa et al, 1990, Biochem.Interntl. 22:411–418.
Vilkas et al, 1986, Biochimie 68:1123–1127.
Wozniewski et al, 1990, Carboyhydrate Research 198:387–391.
Yagi et al, 1977, Planta Medica 31:17–20.

* cited by examiner

*Primary Examiner*—James O. Wilson
*Assistant Examiner*—Leigh C. Maier
(74) *Attorney, Agent, or Firm*—Akin, Gump, Strauss, Hauer & Feld, L.L.P.

(57) ABSTRACT

The present invention provides a method of isolating mucilaginous polysaccharides from plants, cereals, cell cultures, or fungi such as mushrooms known to have mucilaginous or protein-bound polysaccharides with desirable biological properties. The mucilaginous polysaccharides present in aqueous solution or tissue extracts are treated with tannins to form a complex which is then separated from the solution. The complex is then treated one or more times with either solvents or other substances in solution to remove the bounded tannins from the complex thereby and releasing the isolated polysaccharide. The polysaccharides prepared according to the present method retain properties that are substantially similar to those of the native polysaccharide as it is found in the respective plant or cell. The polysaccharides thus prepared are used in a variety of products. This process is particularly suitable for isolating acetylated mannose polymers from aloe plants and beta glucans.

51 Claims, 4 Drawing Sheets

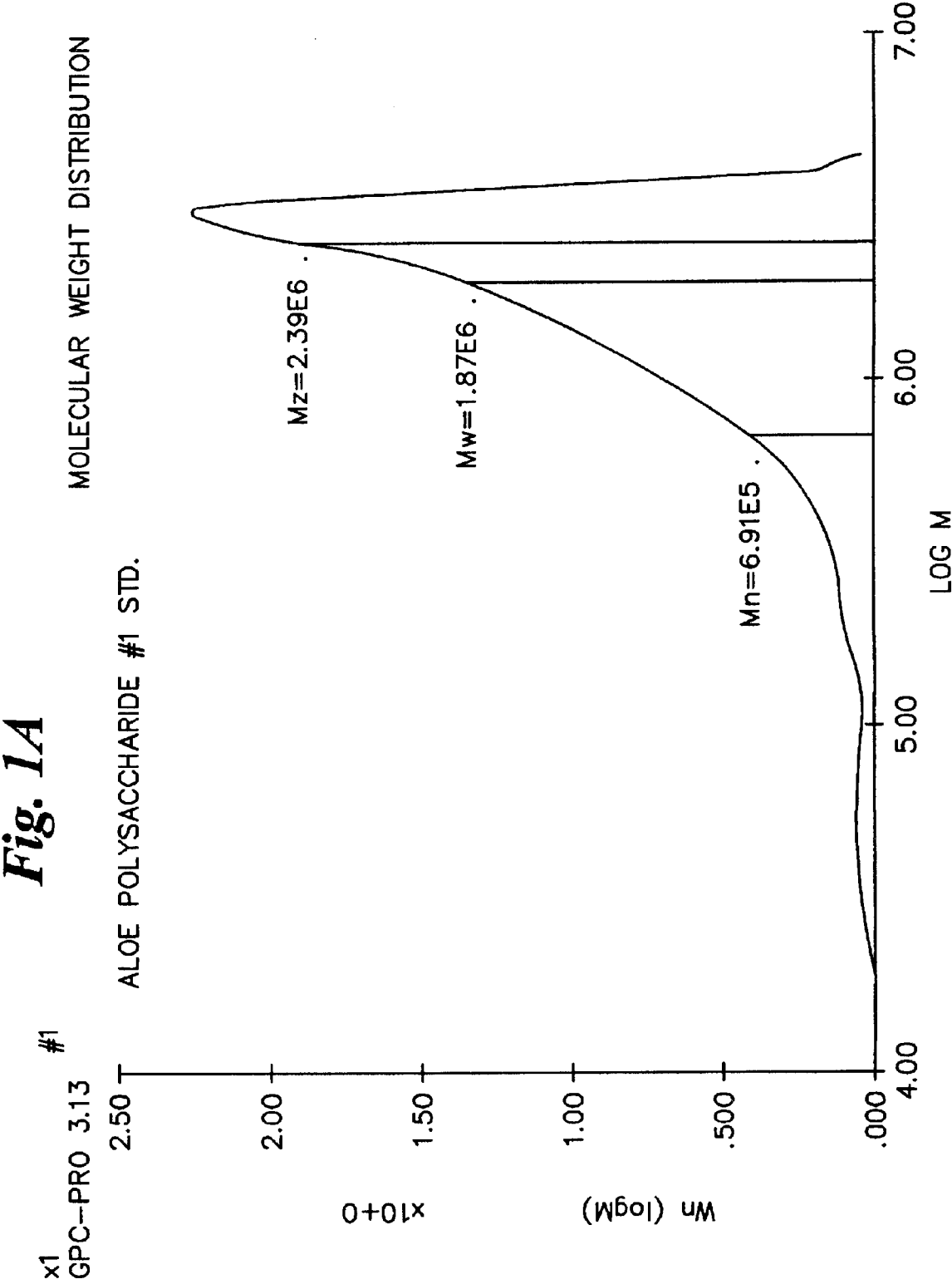

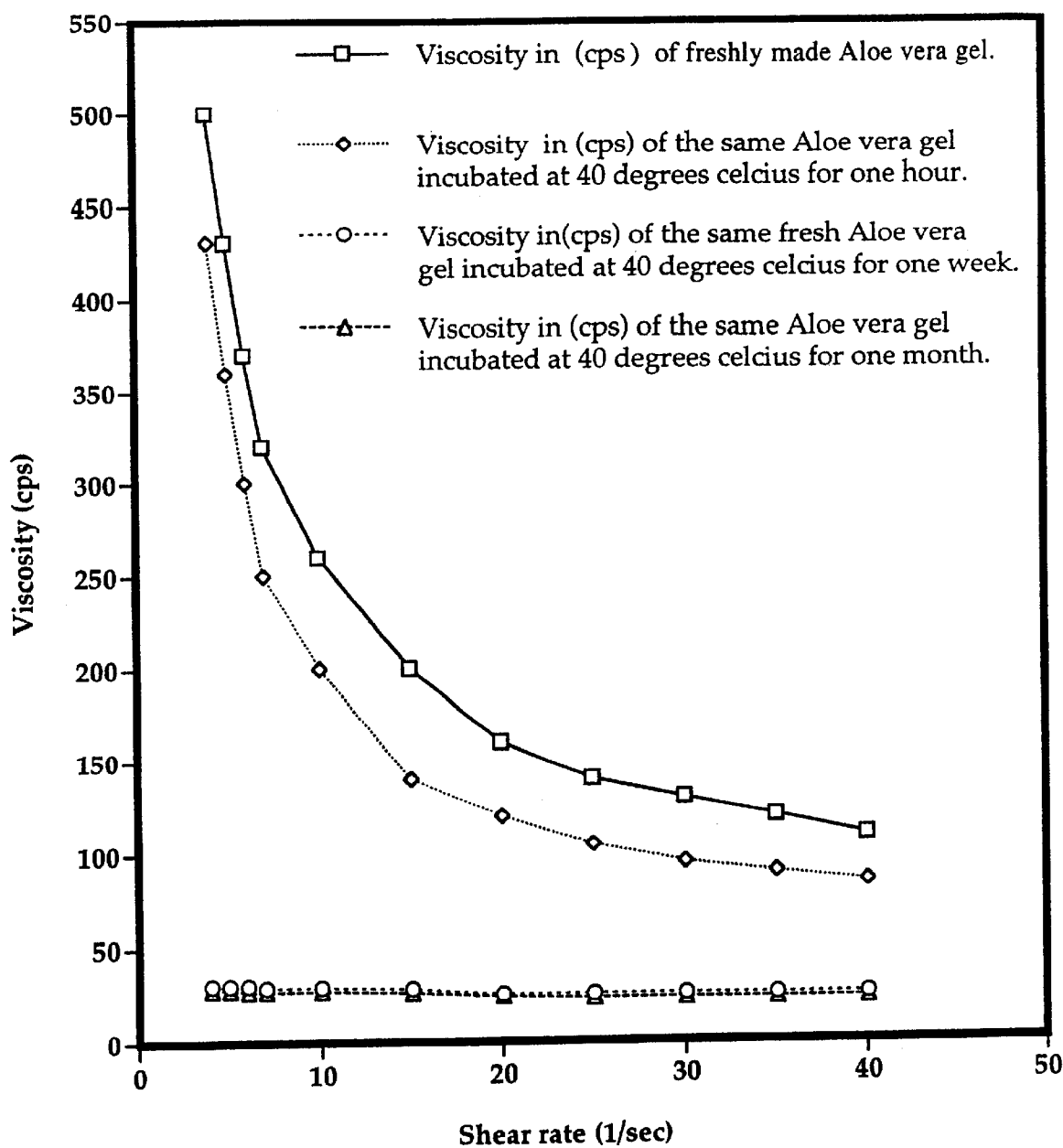
FIG. 2 : Representation of the viscosity profile versus shear rate of Aloe vera gel at different stages of time. Viscosimetry measuraments made using a Haake Rotovisco viscometer equiped with coaxial cylinders MV1 and SV1 sensors, and a MK50 measuring head.

METHOD OF ISOLATING MUCILAGINOUS POLYSACCHARIDES AND USES THEREOF

CROSS-REFERENCE TO EARLIER FILED APPLICATION

This application claims the benefit of co-pending priority U.S. patent application Ser. No. 60/115,619 filed Jan. 12, 1999.

FIELD OF THE INVENTION

This invention relates to the use of tannin related compounds for the selective extraction and purification of mucilaginous polysaccharides from biological materials such as plants, ground biological tissues, or fermented cultured broths from microorganisms. In particular, this invention relates to the precipitation of acetylated mannose polymers derived from the aloe plant and beta glucans from oats and fungi.

BACKGROUND OF THE INVENTION

Generally speaking, mucilaginous polysaccharides are defined as biopolymers characterized by hetero or polysaccharide chains, either linear or branched, having acetyl, nitrogen acetyl, or other nitrogen functional groups associated with the main polysaccharide chain, and containing protein chemically bound to one or more of the external OH groups of the main structure of the polysaccharide chains. Some of these mucilaginous polysaccharides are immunomodulators, and their biological and physical properties make them useful in a variety of applications as ingredients for cosmetics, beverages and pharmaceuticals and as viscosifiers in several multiple chemical production processes. Because of their complex native chemical structure, mucilaginous polysaccharides tend to form a colloidal network with other substances present in solution. It is difficult to separate or isolate these substances while at the same time retaining most or all of their native properties.

Aloe polysaccharides are known as acetylated hetero poly-mannose biopolymers having about one or more acetyl groups per saccharide. (Manna S., McAnalley B.H.; "Determination of the position of the )O-acetyl group in a beta-(1→4)-mannan (acemannan) from Aloe barbadensis miller". *Carbohydrate Research* (1993) Mar 17; 241:317–319). Although the author takes for granted, without any previous carbohydrate analysis, that the sample that he was analyzing was 100% mannan in its composition, he concludes that the O-acetyl groups in Aloe polysaccharides are located at C-2/C-3 position and at C6 position in a 50:50 ratio.

The acetyl group : saccharide ratio in aloe polysaccharides can also vary with the age of the source plant and other environmental factors, but in general terms the plant in its natural state typically maintains the inner biopolymer with an acetyl group : per saccharide ratio of 1 or higher, wherein the polysaccharide is composed mainly, but not entirely, of mannose. It is believed that the biological and physical characteristics of aloe polysaccharides are attributable in large part to the presence of acetylated mannose residues. This biopolymer is different thanother poly-mannans such as locust bean gum or guar gum which have no reported immunological biological activity.

Mucilaginous polysaccharides have traditionally been isolated either by the use of organic solvents, the use of ammonium sulfate, quaternary ammonium salts and by the use of cationic detergents. However, some of these procedures tend to alter the initial chemical structure of the native biopolymer.

Polysaccharides and mucilaginous polysaccharides will generally form viscous solutions or dispersions exhibiting a typical non-newtonian viscosity profile in polar solvents due to hydrogen bonding (R. L. Whistler, "Industrial Gums"R. L. Whistler and J. N. B. Miller, eds. Academic Press Inc., New York, N.Y., 1959, p 1). Because of the general inability of polysaccharides to swell in organic liquids such as ethanol, methanol, or acetone, these organic solvents traditionally have been used to precipitate polysaccharides from their carrier solutions. However, aside from requiring large amounts of solvent, the solvent precipitation technique tends to provide, co-precipitation of other materials such as organic acids, certain salts, proteins, and other similar substances, giving low product yields and/a somewhat degraded biopolymer.

Ethanol is generally preferred for precipitating the mucilaginous polysaccharides network from aloe vera and other similar mucilages and polysaccharides. Typically, aqueous solutions or extracts of the mucilaginous polysaccharides are treated with five or more volumes of ethanol (U.S. Pat. Nos. 4,957,907, 4,917,890, 4,735,935) to precipitate the polysaccharide. This ethanol-based method of precipitating aloe polysaccharides tends to yield a final polysaccharide product having a significantly reduced acetyl group total saccharide ratio, which is different than the initial native chemical structure, and to denature the glycoproteins present in the hydroparenchima of aloe vera leaves. The reduced acetyl group: saccharide can be attributed to a variety of factors such as the time required for making the gel of aloe allowing enough time for hydrolytic enzymes present in the hydroparechima to act on the polysaccharide, and for the normal increase in temperature caused by the addition of ethanol to the aqueous extract. The second technique for isolating mucilaginous polysaccharides requires the use of large quantities of ammonium sulfate or quaternary ammonium salts to precipitate all the polysaccharides. Detergent cations, such as cetyltrimethylammonium (CTA) or cetylpyridium (CP) also have the ability to form insoluble salts with hydrophobic polyanions, and these insoluble salts then precipitate out from their aqueous solution (J. E. Scott, Chem and Industry (London) 1568 (1955), and A. S. Jones, Biochem. Biophys. Acta, 10, 607 (1953)). The use of CTA and other similar detergent cations for precipitating polysaccharides is another example of structural polysaccharide alteration. Dupont showed that different angiogenic biological activities were obtained from different samples of shark cartilage mucopolysacchardie recovered from initial water extracts, which were treated with different precipitation techniques. After in vivo and in vitro examination, only those shark cartilage mucopolysaccharides which were obtained using the technique of water extraction followed by molecular ultrafiltration, were able to show significant biological activity as compared with other shark cartilage polysaacharide samples obtained either by the classical solvent preciptation using ethanol or using detergent cations (Dupont,Eric et.al., U.S. Pat. No. 5,618,925: "Extracts of shark cartilage having an anti-angiogenic activity and an effect on tumor regression; process of making thereof." Apr. 8,1997).

Another commonly used procedure for recovering polysaccharides is the use of ammonium salts. However this procedure works best when individual samples containing polysaccharides have similar ionic character. However, some biopolymers present in certain biological extracts often contain various varieties of polysaccharides, which can vary widely in ionic character. This variability makes the use of ammonium salts unsuitable for application in biological extracts containing heterogeneous types of biopolymers.

Tannins have been classified chemically either as (1) condensed tannins (known as proanthocyanidins), which are chemically defined as flavanoid-based polymers, or (2) hydrolyzable tannins (Haslam E., (1981). Vegetable tannins. In Conn, EE (ed.): "The biochemistry of plants Volume 7," New York Academic Press, p 527–556. In the case of condensed tannins, the beta ring of the flava monomer is generally substituted with two or three ortho-hydroxyl groups. An example of a condensed tannin is the one found in the testa of the grain Sorghum bicolor. On the other hand, hydrolyzable tannins are characterized by a polyhydroxy alcohol esterified with gallic acid (3,4,5-trihydroxybenzoic acid). Hydrolyzable tannins include the family of substances known as ellagitannins and gallotannins which, upon acid hydrolysis, give rise to ellagic and gallic acid. The typical commercial form of hydrolyzable tannins is known as tannic acid. It is well known that hydrolyzable tannins tend to form insoluble complexes with proteins. These complexes are generally water insoluble, but they can be dissociated by various techniques including solvation with organic solvents. Both condensed and hydrolyzable tannins can form insoluble complexes with biological protein-polysaccharide colloidal networks under certain conditions.

Four distinct mechanisms have been proposed to describe the chemistry of the interaction between proteins and tannins. These mechanisms are based on covalent interactions, ionic, and hydrogen bonding or hydrophobic interactions. Covalent interactions may result from nucleophilic attack of amino acid side chains such as lysine on the quinonoid oxidation products of tannin. (O-quinones formed in plant extracts, their reaction with amino acids and peptides. Pierpoint W E (1969), Biochem J. 112 : 609–618.) Such reactions occur most readily at high pH, where oxidation of the phenolic group is most likely. Ionic interactions between cationic amino acid side chains such as lysine and the phenolate anion occur only at pH values greater than the pKa of the phenolic hydroxyl group (pKa=9–11). Loomis W. D. (1974), "Overcoming problems of phenolic and quinones in the isolation of plant enzymes and organelles". Meth Enz 31: 528–544. The most common mode of interaction between tannin and protein involves hydrogen bond formation between the protein amide carbonyl and the phenolic hydroxyl. (Hagerman A. E., Butler L. G. (1980), "Condensed tannin purification and characterization of tannin-associated protein"J. Agri Food Chem 28: 947–952.)

The interaction of tannic acid with protein is also pH-dependent, occurring preferably at pH values lower than the pKa of the phenolic groups, and related to its isoelectric point. The aromatic portion of the tannin may interact hydrophobically with non-polar amino acid side chains, such as phenylalanine, and these hydrophobic interactions are generally pH-dependent. The effects of the solvent composition on tannin-protein interactions suggest that complex formation results from hydrogen bonding and hydrophobic interactions. Studies on the interaction between condensed tannin and bovine serum albumin (BSA) showed that the complex includes strong non-covalent bonds. This complex can not be dissociated by strong buffers, but it can be disrupted by detergents or hydrogen bonding solvents.

Tannins have been used for the clarification of starch-containing solutions. The interaction of starch, an underivatized polysaccharide, with tannins was reported by Davis and Harvers (David,A. B. and Harbers, L. H.1974. "Hydrolysis of sorghum grains starch by rumen microorganisms and purified alpha-amylase was observed by electron Microscopy". J.Animal.Sci., 38:900). They reported that starch prepared by wet milling of bird resistant sorghum was less susceptible to the attack by enzymes than other starches. They suggested that absorption and retention of condensed tannins on starch might be responsible for this phenomenon. Tannins are known to associate with Sephadex™ chromatographic gels. The complexation may be due to inclusion of phenolics within the pores of Sephade™, interactions between oxygen atoms from ether groups that crosslink the gels, phenolic hydroxy groups as well as interactions between the phenyl ring acting as an electron donor and the hydroxy groups of gels (Brook,A. J. W. and Munday,K. C. 1970; "Interactions of phenols, anilines and benzoic acids with Sephade™ gels". J. Chromatogr., 47:19.) Tannins have also been reported to have a strong affinity towards cyclodextrins, and polygalacturonate. Ozawa reported that starch, such as amylose, can develop a secondary structure containing hydrophobic cavities. Also polyamides, such as polyvinylpyrrolidone, non-ionic detergents, polyethylene oxides, and alpha, and beta cyclodextrins and alkaloids such as caffeine and cinchonine, associate strongly with polyphenol substrates (Ozawa, T. et.al. 1987. "Polyphenol Interactions : Astringency and the loss of Astringency in ripening fruit". Phytochemistry, Vol. 26, N.11, pp.2937–2942.).

Non of the prior art to date has reported on the specific interactions of tannins with Aloe polysaccharides and protein bound-beta-glucans. Accordingly, the prior art has not overcome the disadvantageous deacetylation that generally occurs during processing of aloe polysaccharides as an acetylated poly-mannose polymer, free of bound malic acid and insoluble material and for the other cases of biologically active polysaccharides. The prior art neither discloses nor suggests that tannins can be used to precipitate the polysaccharides of aloe and especially the aloe acetylated mannose polysaccharides having the particular properties described herein. Further, the prior art does not disclose or suggest an aloe-derived polysaccharide having the properties described herein.

SUMMARY OF THE INVENTION

The present inventor has discovered that mucilaginous polysaccharides, such as the acetylated poly-mannose in aloe, and other similar polysaccharides such as beta-glucans produced by plants or poly-glucans produced by cultured microorganisms can be separated from solutions or aqueous extracts by complexation with tannins and specifically with hydrolyzable tannins. The present invention provides a superior method for the isolation of mucilaginous polysaccharides from a wide variety of plant and cell culture sources, especially those derived from aloe plants. The mucilaginous polysaccharides made according to the invention have properties that are improved over those mucilaginous polysaccharides made according to other known processes. The present invention, in particular, provides a process for isolating mucilaginous polysaccharides retaining most, if not all, of their native properties. The claimed invention also provides a process for the preparation of high quality mucilaginous polysaccharides in high yields. Further, the present process does not require large volumes of organic solvents as for the classical process employing ethanol, and in some embodiments, organic solvents are entirely eliminated from the process.

In one aspect the present invention is a method of isolating a mucilaginous polysaccharide comprising the steps of:
  a) adding a first aqueous solution containing 0.5 to 10% weight/volume of hydrolizable or condensed tannins to a second aqueous solution containing polysaccharides or protein-bound polysaccharides while mixing to form a first insoluble complex composed of tannins and polysaccharides or biopolymers;

b) separating the complex from aqueous solutions to form a first water insoluble tannin-polysaccharide complex; and c) breaking the tannin-biopolymer complex either by the use of solvents such as methanol, ethanol, methanol, butanol, acetone, 1,3 dioxalane or mixtures of these solvents with water with or without PEG and Tween 80; or d) breaking the tannin-biopolymer complex by the use of water solutions containing either PVP, PPVP, casein, albumin, gelatin or other similar protein sources.

In some preferred embodiments, the solution of tannins is prepared by:

1) using an acetone: water extract made by gel permeation chromatography using Sephade™ L-20 where commercially available tannic acid or other forms of Hydrolizable tannins are used as starting material. The ratio of acetone: water for elution of ellagotannins varies from 10: 90 up to 80: 20 and works best between 50:50 and 75:25; or 2) using an acetone : water extract made by classical chromatography using typical silica adsorbent materials and using tannic acid or other forms of tannins as starting material.

The present method can also comprise one or more of the following steps:

e) removing all tannins from the insoluble tannin-polysaccharide mass by the use of solvents to form a second mass of aloe biopolymers free of bounded tannins;

f) reducing the ionic strength of the Aloe gel extract by the use of specific resins prior the addition of the tannic acid;

g) dissolving the isolated tannin free polysaccharides in water to form a viscous solution containing the polysaccharide in a concentration ranging from 0.2% up to 0.6% weight/volume;

h) adding a preservative such as sodium benzoate or potassium sorbate to said aqueous solution;

i) reducing the particle size of solids in the first and/or second mass by means of special desintegrator/ homogenizer equipment;

j) adding saline water, Tween 80, sodium sulfate, gallic acid or n-propyl-gallate to the second solution prior to the addition of the first solution containing tannins;

k) treating the first mass one or more times, optionally with mixing, with a sufficient amount of one or more solutions containing at least one of a surfactant and a glycol polymer to remove a major portion of the tannin from the mass to form a second mass having properties similar to the initial native polysaccharide;

l) using an acetone-water extract of ellagitannis made by treating commercially available tannic acid or other sources of tannins, with gel permeation chromatorgraphy or using classical chromatography techniques using other adsorbent type of packing materials, to complex the mucilaginous polysaccharides; and/or m) using ellagitannins that have been extracted from the original tannic acid powder or other sources of tannic acid by the use or chromatography or gel permeation chromatography by using Sephadex™ L-20. The ellagitannins extract contains at least one selected from the group consisting of the group chemically known as Nobotanins, Corilagins, Gemins, Augosin, Rugosin, Isorugosin, Corousilins, Coriariums, Ocnotheins, Agrimonin, Geraniin, Granatin and Cornusiins.

Another aspect of the invention provides a polysaccharide prepared according to the process described herein. In this aspect, the invention provides a polysaccharide isolated from plant extracts or produced by cell cultures, wherein the polysaccharide possesses properties which are about the same as those of the polysaccharide as it is found in the native plant or cell culture. In a preferred embodiment, the invention provides a polysaccharide isolated from an aloe plant, wherein the polysaccharide has at least one of a weight average molecular, an acetyl group: saccharide ratio, a saccharide content, a saccharide end group content, and a linkage group analysis similar to that of the polysaccharide as it is found in the native aloe plant.

The aloe-derived polysaccharide isolated according to the present invention generally possesses an acetyl group : saccharide ratio of about 1:1 or higher and is a high molecular weight polysaccharide. The molecular weight distribution of the isolated polysaccharide is generally broad and in the range of 10,000 up to 1,700,000. The aloe-derived polysaccharide isolated according to the present invention generally comprises arabinose, rhamnose, xylose, mannose, and glucose present in amounts similar to those found in the native plant, and preferably in amounts in the range of about 0.8–1.2% wt. of arabinose, 0.08–0.35% wt. of rhamnose, 0.35–045% wt. of xylose, 80–85% wt. of mannose, and 14–18% wt. of glucose based upon dry weight of the polysaccharide. The saccharide end group content and linkage group analysis of the polysaccharide isolated from aloe using the process of the invention generally yield the following results:

1.-Terminal arabinose (furanose): 0.7;

2.-Terminal xylose : 0.0;

3.-Terminal mannose: 0.9;

4.-Terminal galactose: 0.5;

5.-4-xylose: 0.7;

6.-4-mannose: 69.6;

7.-4-glucose: 9.7;

8.-3,4-mannose: 4.0;

9.-2,4-mannose: 2,5;

10.-2,3,6-mannose: 2,3;

11.-4,6-mannose: 5,4;

12.-4,6-glucose : 0.5;

13.-3,6-galactose: 1,4;

14.-3,4,6-mannose: 0.8;

15.-2,4,6-mannose: 0.8; and

16.-2,3,4,6-mannose: 0.7.

A variety of tannin compounds can be used in the process of the invention. Hydrolyzable tannins are preferred for the isolation of mucilaginous polysaccharides from aloe. Selection of a preferred tannin compound for isolating a particular type of polysaccharide generally depends upon the identity of the polysaccharide and the reaction conditions employed. Tannic acid is generally preferred for complexing mucilaginous polysaccharides from aloe.

Based upon the chemical affinity and specificity of the binding of condensed and hydrolyzable tannins to proteins and nitrogen acetyl functional groups present in mucilaginous polysaccharides, a particular polyphenol, proanthocyanin, gallatannins, ellagitannins (referred to as hydrolyzable tannins) will be preferred for isolation of the mucilaginous polysaccharides. In general about 1 gram of Aloe polysaccharide in solution will bind about 0.5 to 1 gram of tannic acid. However, this relation is not the same when an acetone : water 50:50 extract of Ellagotannins eluted out of a Sephadex™ LH-20 column is used instead. In the latter case, about 1 gram of the Aloe biopolymer network will generally bind with about 0.02 to 0.3 g. of ellagitannins. The ratio in which tannins bind to specific polysaccharide depends upon many varibles and a stoichiometric relationis not required.

The polysaccharides isolated from plants, cereals, fungi or cell cultures according to the invention are used in a wide range of products. Accordingly, the present invention provides a composition comprising an aloe-derived polysaccharide isolated by a process using a tannin, said composition being present in at least one of a beverage, candy, comestible, tonic, lotion, cosmetic, pharmaceutical composition, suppository, implant, shampoo, hair conditioner, wound dressing, wound or injury treatment product, anti-itch formulation, sun-burn formulation, topical formulation, oral formulation, dietary composition, food supplement, injectable formulation and other products known to those of skill in the aloe art.

Other features, advantages and embodiments of the invention will be apparent to those of ordinary skill in the art from the following description, examples and appended claims.

BRIEF DESCRIPTION OF THE DRAWINGS

The following drawings form part of the present specification and are included to further illustrate certain aspects of the invention. The invention can be better understood by reference to one or more of the drawings in combination with the detailed description of the specific embodiments presented herein.

FIGS. 1a–1c depict size-exclusion HPLC chromatograms of mucilaginous polysaccharides isolated from aloe and, in particular, a commercially available polysaccharide named MANNAPOL™ (FIG. 1c), the native Aloe polysaccharide isolated directly from the aloe inner hydroparenchyma (FIG. 1a) purified by the use of the procedure similar but with some variations to the one described according the procedure published by L.A.'tHart, et al. ("An anti-Complementary polysaccharide with Immunological Adjuvant Activity from the Leaf Parenchyma Gel of Aloe vera." Planta Medica 55 (1989) pages 509–512), and a polysaccharide isolated according to the invention and described as Vito-Mannnan (FIG. 1b). The experimental conditions for the HPLC analyses were run generally as follows:

Columns: Ultrahydrogels: 2000A+1000A

Solvents: Water (0.05 M NaNO3)

Figure 1B:
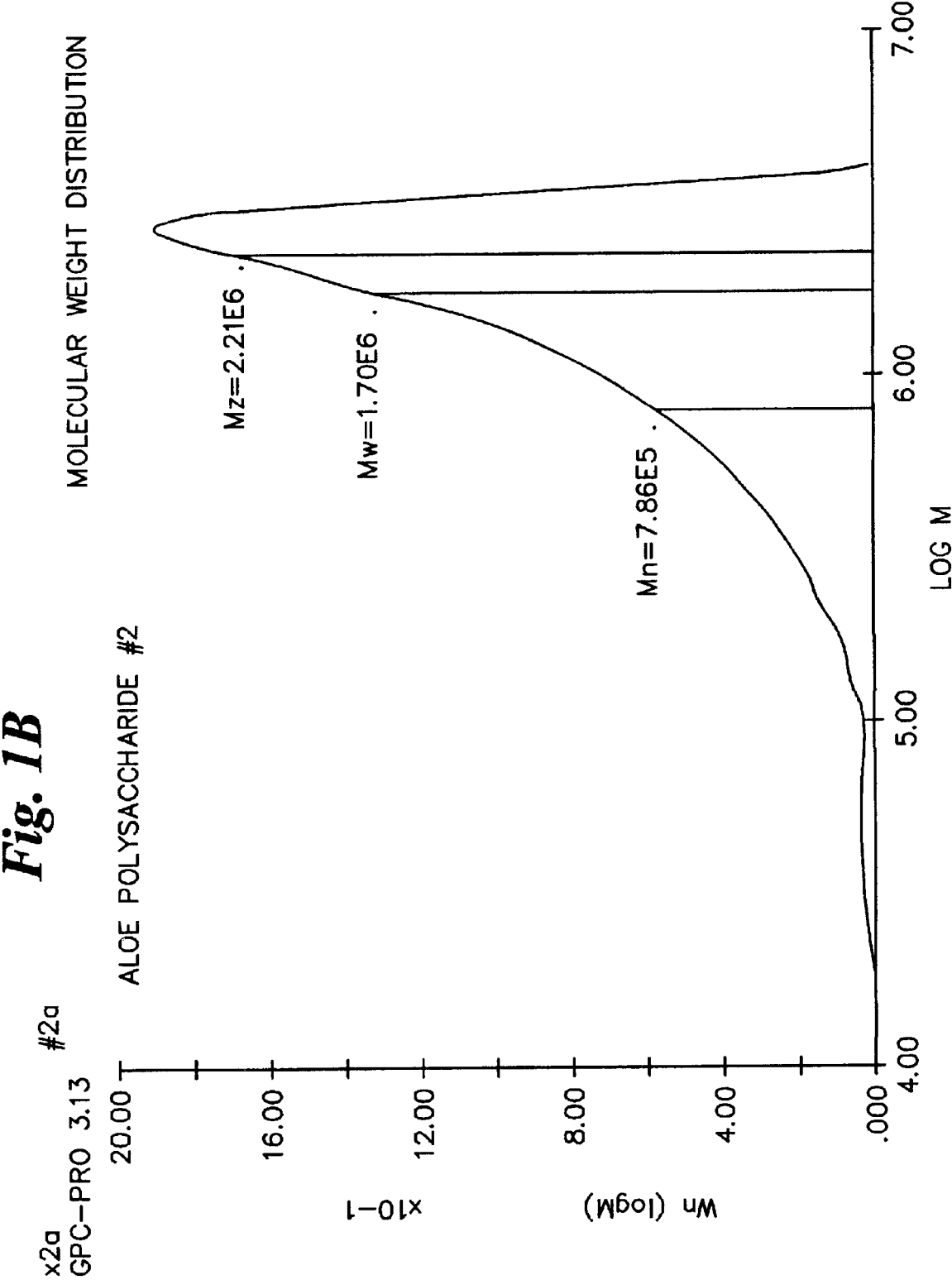

Temperature: 30 degrees celcius.

Flow rate: 1.0 ml/min.

Injection Volume: 100 microliters.

Detectors: Knauer DRI at 8×.

Data Module: GPC PRO 3.13 IBM AT.

FIG. 2 depicts a plot of viscosity versus time for a native aloe polysaccharide exposed to hydrolytic enzymes at a slightly elevated temperature.

DETAILED DESCRIPTION OF THE INVENTION

Without being held to a particular mechanism, it is believed that complexation of mucilaginous polysaccharides with tannins involves several chemical mechanism such as hydrophobic and hydrogen binding. The bound tannin and polysaccharide form an insoluble complex that resembles an amorphous filamentous mass. This amorphous filamentous first mass is then separated from the supernatant and subsequently purified.

A general procedure according to the invention for isolating a mucilaginous polysaccharide is conducted as follows. An aqueous solution, fungy mycelia extract, or cell free fermented broth containing the polysaccharide is mixed for a period of time with a suitable quantity of a tannin solution containing tannin in a concentration which varies from 0.5 up to 10% weight/volume at a suitable pH. If an ellagitannins extract is used, the ratio is generally reduced to only 0.1 to 0.5% weight/volume in water. After the addition of tannins to the aloe extract, the solution is mixed and allowed to stand for a period that varies from 1 up to 15 minutes. After this first period is complete, a polysaccharide/tannin complex has formed which by hydrodynamic force tends to suspend in solution. The separation also depends upon the quantity of free water available and the hydrodynamics of the complex formed, which varies according to the polysaccharide being isolated and the particular tannin used for the extraction. The complex resembles an aggregate amorphous solid which is then separated from the solution either by centrifugation or decantation. The solid is then desintegrated and then treated with a first wash composed of an acetone-water mixture having a 70:30 to 85:15 acetone-:water ratio, taking in consideration that the water in this wash mixture includes the water that is associated with the tanni/polysaccharide complex. The ratio of solvent/water varies according to the amount of free water associated with the complex. The water part may also contain some other substances. After an initial wash with water, the complex is washed two or more times with the acetone-water mixture until little to no tannin is detected in the wash solution. The remaining solid mass is then finally rinsed with ethanol to remove water and dried under vacuum.

The pH of the solution containing the tannin and the polysaccharide is controlled to improve yield and/or purity of the complex formed. The pH is generally in the range of 3 to 5, and preferably in the range of 4.3 to 4.5 for the isolation of aloe derived polysaccharides when hydrolyzable or ellagitannins are used. If a higher pH is used in the range of 5.5 to 7,0 and preferably at 6.8, the acetyl group: saccharide ratio tends to decrease a little and the yield increases slightly. The product isolated at higher pH values has more associated protein than the product isolated at pH of 4.5.

The preferred temperature of the solution containing the tannin and the polysaccharide is generally about room temperature in order to reduce degradation of the polysaccharide, improve complex formation, or improve yield and/or purity of the complex. The temperature is generally in the range of 25 to 27 degrees celcius and generally not higher than 30.

The weight ratio of hydrolyzable tannin to native polysaccharide dissolved in the original solution used to form the complex will vary according to the type of tannin utilized to form the initial insoluble complex. For the specific case of Aloe, when commercial hydrolyzed tannins, sold as tannic acid, are employed, the ratio of polysaccharide or biopolymer: tannic acid generally varies between 1: 0.5 to 1.3 w/w, and preferably is preferably about 1:1 w/w. However, when extracts of ellagitannins are made from Tannic acid using gel permeation chromatography or other similar chromatographic technique using other adsorbent types of materials, then the ratio is lower and generally in the range of about 1: 0.03 to 0.5 w/w and preferably about 1:0.25.

The present invention provides a process wherein the extent of the typical enzymatic depolymerization or deacetylation of aloe gels is reduced as compared to other processes. In order to illustrate the enzymatic depolymerization of Aloe gels, FIG. 2 illustrates the change in viscosity of Aloe vera gel when the aqueous extract is subjected to an incubation at 40 degrees celcius at different times periods. About one hour after the gel is made, the enzymatic degradation and the change is viscosity is quite evident. After one week, the original aloe vera viscosity profile has changed totally its original non newtonian Theological character is reduced to a simple newtonian character where the shear rate vs shear stress is a straight line, as is the case for water. The addition of tannic acid into water extracts of the hydroparenchima of aloe vera leaves allows for the total complexation of tannic acid with all biopolymers present and some other nitrogen base substances present in the Aloe water extract. The presence of the pholyphenols apparently inhibits the action of hydrolytic enzymes responsible for the degradation of the aloe polysaccharide. The process also reduces or eliminates the enzymatic degradation of beta glucans, which typically occurs during their isolation using other processes, particularly for beta glucans present in oats where beta-glucanase enzymatic degradation also occurs. For the case of Aloe polysaccharides, the present process helps to prevent not only the biopolymer degradation but also to preserve the aloe's acetyl group:saccharide ratio at a level approximating that found in the native plants.

When tannic acid is used, the weight ratio of washing solvent mixture to initial wet tannin/polysaccharide complex will vary according the amount of water associated with the first mass of tannin/polysaccharide recovered after the addition of tannin to the Aloe vera gel. Generally this ratio of washing solvent mixture: insoluble tannin-polysaccharide varies within 4 :1 and is preferably about 2.5 parts of washing solvent mixture: 1 part of tannin/polysaccharide complex. The washing solvent may comprise a single solvent and water or a mixture of solvents and water. The solvent mixture may also be formed by a mixture of single solvents or a mixture of solvents and water. For this case, the ratio varies between about 60:40 and preferably about 70:30. The water portion may be distilled water or a solution made of distilled water and PEG and Tween 80. The concentration of PEG the water part may be in a concentration of 1 up to 5% weight/volume and preferably about 3% w/v. The preferred types of PEG used have molecular weights ranging from 2000 up to 8000, and the more preferred form is the PEG 8000. The amount of Tween 80 present in the water part of the washing solvent is of 0.01 to 0.05% and preferably about 0.02% weight/volume of the water portion in combination with the PEG. When ellagotannin extracts made from tannic acid are used, the weight ratio of washing solvent mixture to initial wet tannin/polysaccharide complex will also vary according the amount of water associated with the first mass of tannin/polysaacharide recovered after the addition of tannin to the Aloe vera gel. Generally this ratio varies within 3: 1 and is preferably 2:1. The washing solvent may be composed by a single solvent and water or a mixture of solvents and water. The washing solvents mixture may also be formed by a mixture of single solvent or mixture of solvents and water. For this case the ratio also varies between 60:40 and preferably 70:30. The water portion may be distilled water or a solution made of water and PEG and Tween 80. The concentration of PEG the water part may have a concentration of 1 up to 5% weight/volume and preferably at 3% w/v. The types of PEG used will generally have a molecular weight ranging from 2000 to 8000 and the preferred form is the PEG 8000. The amount of Tween 80 in the water part of the washing solvent is of 0.01 to 0.05 and preferably at 0.02% weight/volume of the water portion. The temperature at which the complex is washed with a solution to remove the tannin is generally at or below room temperature. Higher temperatures should generally be avoided to minimize polysaccharide degradation. It is generally preferred that the wash step be conducted at about 28° C.

The process of the invention can be conducted in commercially available equipment including, for example, reactors, mixers, filters, dryers, tanks, separators, conveyors, conduits, particle sizers and others known to those of skill in the chemical arts. The process can be conducted as a continuous, semi-continuous or batch-type process. One or more of the process steps may require heating and/or cooling. Such heating and/or cooling can be performed using heat exchangers, jacketed vessels or conduits and other such equipment known to those of skill in the chemical process arts. In preferred embodiments, exposure of the polysaccharide to excessive heat will be minimized to reduce the occurrence of degradation.

Essentially any plant or cell culture containing mucilaginous polysaccharides can serve as the source of materials used in the invention. Exemplary sources of mucilaginous polysaccharides include leaves of the aloe plant, extracts of Plantago ovata, Plantago major, protein-bound polysaccharide from mycelia or fruiting bodies of medicinal mushrooms such as Coriolus versicolor, Shiitake (Lentinula edodes), Maitake (Grifola frondosa), the Reishi/Ling Chi Mushrooms (Ganoderma lucidum), and Glucans present in cereals such as oats enriched with 1–3,1–4 beta-D-glucans. The mucilaginous polysaccharides that can be isolated according to the invention include: 1–3,1–4 beta glucans, acetylated polymannans, mucilages with main chain composed of Beta 1–4 acetylated D-xylopyranose residues, galacto-mannans such as the ones from Cassia Augustifolia, and protein bound water soluble 1–3 beta -D -glucans from mushrooms.

Tannins are well known compounds which are available from many commercial sources. All tannins can be used according to the invention depending upon the source of polysaccharide used, the polysaccharide to be isolated, and the process conditions used. Generally speaking, tannins include (1) condensed tannins (known as proanthocyanidins), and (2) hydrolyzable tannins. Any tannin may be used so long as it has gallic acid residues attached as constituents. Hydrolyzable tannins such as gallotannins such as the Chinese gallotannins,turkish gallotannin, tara gallotannin and similar ones are also useful. Ellagitannins available from myrobalan, divi divi, chesnut, and similar ones are also useful. All of these tannins and their derivates are well described in detail in the *Journal of Scientific and Industrial Research*, (vol 41, December, 1982 pp 705–718) and also in the Japanese publication Yakugaku Zasshi (103 (2), 125–142 (1983)). Of these tannins, Chinese gallatonnin, tara tannin and the commercial forms of tannic acid, which are hydrolyzable tannins, particularly preferred materials from the point of view of their supply and price. However, when acetone fractions extracted from commercial available samples of tannic acid are made according to the technique of gel permeation chromatography using Sephade™ LH-20, ellagitannins yield a product with is easier to handle and less colored. All of these tannins will form substantially water-insoluble complexes with mucilaginous polysaccharides, which can be dissociated by one or more techniques including solvation with organic solvents and disruption with some protein polymers or a surfactant or a glycol polymer.

In the present invention, tannins can be removed from a mass comprising a polysaccharide and the tannin by treating the mass one or more times with one or more solvents or mixtures of solvents. Solvents which are useful according to the invention are those which can dissolve or solvate the tannin. The solvents can be water miscible or water immiscible; although, water miscible solvents are preferred. Suitable solvents include acetone, methanol, ethanol, isopropanol, butanol, 1,3 dioxalane or mixtures thereof and aqueous mixtures thereof Tannin can also be removed from the polysaccharide/tannin complex with materials including: 1) proteins such as albumin, casein, gelatin, and animal hide powders; 2) powdered nylon such as ULTRAMID™; 3) soluble or insoluble poly(vinlypyrrolidones); 4) polystyrenes; 5) polyacrylates such as AMBERLITE™ XAD-2, XAD-4, XAD-7; 6) phenol specific resins such as DUOLITE™ XAD 761 from Rohm & Haas; 7) cation exchange resins such as DOWEX™ 50 and DOWEX™ 100; 8) anion exchange resins such as BIO-RAD™AG1-X8, BIO-RAD™ AG2-X8, and DOWEX™1; 9) glycol polymers such as poly(ethylene glycol) (CARBOWAX™ 8000 from Union Carbide); 10) surfactants or detergents such as poly(oxyethylene sorbitan monooleate) (TWEEN™ 80 from Union Carbide); and 11) combinations thereof. These materials can be used in aqueous or non-aqueous solutions to remove the tannin. In a preferred embodiment, a surfactant and a glycol polymer are used to remove the tannin from the polysaccharide/tannin complex. In another preferred embodiment, a surfactant, a protein and a glycol polymer are used to remove the tannin from the polysaccharide/tannin complex. In another preferred embodiment, a solution containing polyethylene glycol, TWEEN™ 80, gelatin, and albumin, are used to dissociate the polysaccharide/tannin complex without using organic solvents.

In order to enhance the shelf stability, minimize microbial contamination, reduce degradation or minimize loss of the desirable properties of the polysaccharide prepared according to the invention, one or more preservatives can be added to their aqueous solutions containing the polysaccharide such as Sodium Benzoate and Potassium Sorbate.

The polysaccharide/tannin complex that is formed by the present invention is generally water insoluble. The complex, which is sometimes referred to herein as a mass, aggregate or precipitate, may float or rise to the surface of a solution containing the complex, may adhere to an equipment surface, may settle in solution or may remain suspended in the solution. The complex may appear filamentous, granular, particulate, gel-like, waxy, flocculent, aggregated, or otherwise as a light brown solid.

The step of separating the tannin polysaccharide complex, or first mass from the initial solution in which it is in, is conducted in any commercially available liquid/solid separating equipment including a centrifuge, filter, decanter, settling tank, skimmer, or other such equipment which is known by those of skill in the art of separating solids from liquids. In preferred embodiments, the separation is conducted by filtration, centrifugation, decantation or combinations thereof. The preferred equipment is a basket centrifuge or centrifugal decanter.

In order to optimize the removal of tannins at the stage of washing the complex with solvents or the dispersion and hydration of the biopolymer in water, it may be desirable to control the particle size of the polysaccharide/tannin complex. Particle size reduction can be accomplished with any commercially available grinding, milling, jet milling, micronizing, or sieving equipment. Such equipment includes, for example, a jet mill, hammer mill, micronizer, blender, chopper, sieve, grinder, ball mill, or other such equipment known to those of skill in the art of sizing solids. This operation is preferably conducted by the use of a Dispax-Reactor (Ika-Works,Inc., 2635 North Chase Pkwy. SE Wilmington, N.C. 28405–7419).

Solutions of biological materials frequently possess chromophores which give the solution an undesirable color. Usually, the color caused by the chromophores is reduced or removed by treating a solution containing the desired compound with a sufficient amount of a decolorizing agent for a time and at a temperature sufficient to reduce or completely remove the amount of color evident in the solution. Although, it is not necessary to remove the chromophore from the solution in order to remove or reduce the color, it is preferred that the chromophore be removed. The color of the polysaccharide isolated according to the invention can be lightened, reduced or removed by dissolving the polysaccharide in a solution and treating it with a color removing agent such as bleach, borohydride, powdered or particulate charcoal, or a polymeric resin that reacts with, adsorbs, complexes with or absorbs the color-causing agent. In a preferred embodiment, the color is reduced or removed by treating an aqueous solution of the polysaccharide with powdered charcoal, such as NORIT™. The charcoal can be acid-washed, activated, or neutral. Other similar materials are the use of anion resins such as ResinTech SIR-22P designed specifically for tannin removal.

The polysaccharide prepared according to the present invention can be dried to form a solid using any commercial drying equipment including a desiccator, freeze-dryer, vacuum dryer, heated dryer, spray dryer, rotary dryer, tumble dryer, tray dryer, conveyor dryer, mixer-dryer, or a combination of two or more of the above.

The purified polysaccharide can be dried to the desired moisture content to form a solid; however, the purified polysaccharide need not be dried. It can be used wet as a wax, paste, gel, suspension or solution in subsequent processing steps or in making products comprising it.

A variety of the above-mentioned products are made with a polysaccharide prepared according to the invention. Since the polysaccharide as isolated herein retains one or more of the properties found in the native form of the polysaccharide, products that are prepared with the present polysaccharide possess improvements over commercially available products having polysaccharides prepared according to other properties.

Aloe derived polysaccharides are found in products such as beverages, candy, comestibles, tonics, lotions, cosmetics, pharmaceutical compositions, suppositories, implants, shampoos, hair conditioners, wound dressings, wound or injury treatment products, anti-itch formulations, sun-burn formulations, topical formulations, oral formulations, dietary compositions, food supplements, injectable formulations and other products known to those of skill in the aloe art. Improved versions of these same products containing, however, the polysaccharide as prepared herein, can be prepared as described below or using conventional methods well known to those of skill in the aloe art.

Aloe derived polysaccharides are used to treat a wide variety of disorders. It is generally thought that the more similar an isolated aloe polysaccharide is to the native form of the polysaccharide, the more efficacious the aloe polysaccharide will be in treating or curing a particular disorder. Accordingly, the present invention provides improved methods of treating disorders which are responsive to aloe polysaccharide therapy, the improvement comprising administering a reduced but therapeutically effective amount of an aloe-derived polysaccharide prepared by a process that employs a tannin for isolating the polysaccharide. The amount of polysaccharide, prepared as described herein, that is required to provide a therapeutic or beneficial response will be reduced in comparison to that amount of polysaccharide, prepared according to other processes, that is required to provide a similar therapeutic or beneficial response.

Disorders which symptoms can be treated with or which can be cured by the aloe-derived polysaccharide prepared according to the invention include: sun-burn irritation, poison ivy irritation, poison oak irritation, gastric ulcers, wound healing, cancer, viral infection, immuno-suppression, immune deficiency, microbial infection, inflammation, AIDS, neuralgia, ulcerative colitis, tuberculosis, cryptosporidiosis, fungal infection, leukemia, chronic rheumatoid arthritis, acute rheumatoid arthritis, depression, anxiety, alopecia, rheumatic fever, influenza, cystic fibrosis, malnutrition, asthma, lupus erythematosus, allergy, hypercholesterolemia, poisonous animal or insect bites, pre-malignant skin lesions, tumors, Kaposi's sarcoma, hepatic tumor, malnutrition, malabsorption syndrome, multiple sclerosis, chronic fatigue syndrome, measles, inflammatory bowel disease, cutaneous ulcers, pneumocystis carinii infection, herpes, iridovirus infection, poxvirus infection, hepadnavirus infection, orthomyxovirus infection, paramyxovirus infection, and wound cleansing.

The mucilaginous polysaccharides produced using method have been shown to be purer and more concentrated than those derived from existing methods. These mucilaginous polysaccharides can be used in a variety of applications. Some examples of compositions using these are disclosed in the following examples.

EXAMPLE 1

An Aloe barbadensis miller water extract is made using the inner gel present in mature Aloe barbadensis miller leaves. The aloe vera leaves are cut transversally, and the inner gel scrapped, homogenized in a blender along with 350 mL of saline water, depulped, and then filtered under vaccum. After adjusting the pH to 4.5, 1850 grams of the filtered mucilage are mixed for 5 minutes at room temperature with 0.75 grams of sodium bisulfite previously dissolved in 10 ml of water. Then, 75 ml of a 10% w/w solution of tannic acid is added slowly at room temperature under moderate mixing. An amorphous precipitate forms, usually immediately or shortly after the tannic acid is added, and the final solution is mixed gently at room temperature for an additional 10 minutes. In order to verify that little to no polysaccharide (aloe mannose) remains in the liquid supernatant after the formation of the tannic acid-aloe mucilage complex, a colorimetric assay for bioactive polysaccharide detection may be performed according to the procedure developed by Eberendu, Alexis. (Alexis N.R Eberendu et. al., U.S. Pat. No. 5,512,488: "Colorimetric Assay for Bioactive Polysaccharide." Apr. 30, 1996).

The final tannic acid-aloe mucilage complex is removed from the initial solution by filtration and the solid portion is pressed against a nylon cloth to remove water. This final solid is immediately transferred into a dry container and an amount of acetone approximately equal to twice the solid's wet weight is added. This mixture then is homogenized in a blender using brief pulses a few seconds long in order to break the solid into small particles and facilitate the extraction of any adsorbed tannins. After the solid is broken up into shorter segments, the organic liquid or supernatant is decanted. Then 50 ml of a 70:30 (v/v) acetone:water solution is added, and the combination is agitated for about 15 minutes. The washing of the complex is generally repeated until little to no tannins are detected qualitatively in the supernatant. The qualitative detection of residual tannic acid may be done qualitatively by using a standard ferric chloride test or by using the Folin-Denis test method.

Once the tannic acid is removed, the polysaccharide is separated from the acetone: water mixture by filtration, followed by a final wash with pure ethanol. If the final product retains a slight discoloration and its removal is desired, 1500 ml of water may be mixed into the amorphous material until the polysaccharide is dissolved completely, then 5 grams of activated charcoal (available commercially as NORIT) may be added and the combination mixed gently for 45 minutes. At the end of the mixing period the charcoal is filtered and the filtrate is dried, or lyophilized, to yield the final product.

EXAMPLE 2

This process is the same as in Example 1, except that instead of using 75 ml of a 10% solution of tannic acid, condensed tannins from the sorghum bicolor testa were used instead. The yield was 12.7% lower and the amount of solvent employed to remove the associated tannins was 37% higher than that for Example 1.

EXAMPLE 3

This process is the same as in Example 1, except that the two initial washings of the mucilagenous polysaccharide are done using an acetone solution containing 2% w/v of polyethylene glycol Carbowax 8000 based on the weight of solvent, and 0.02% w/w of Tween 80 based upon the wet weight of the tannin-polysaccharide complex. The final was is done without the need to incorporate either the Carbowax 8000 or the Tween 80, followed by a rinse with Ethanol. This technique reduces the total solvent requirement by about 10% and the final vacuum-dried product typically is whiter than that produced using the Example 1 procedure, thus reducing or eliminating the need for the charcoal purification step described in Example 1.

EXAMPLE 4

In this example, the entire aloe vera leaf is used, in contrast with Examples 1 and 2 where only the leaf gel was used. The entire Aloe leaves were ground and the final viscous material separated from the external cellulosic materials by filtration. Then, the process as described in Example 2 was followed in order to process 2 Kgs of the final filtered viscous extract. In this particular case, 95 ml of a 10% w/w solution of tannic acid is used, along with 550 ml of an acetone:water mixture containing polyethylene glycol and Tween 80 in the same percentages and fashion as described in Example 3.

EXAMPLE 5

This example describes a procedure for the disruption of the tannin-polysaccharide complex obtained in Example 1, using a non-solvent approach. To illustrate this technique, 1 gram (wet weight) of the tannin-polysaccharide complex obtained in Example 1 is placed into a of 200 ml beaker. The initial amorphous mass is first desintegrated into small minute particles and then 70 ml of a water solution containing 3% weight/volume of Carbowax™8000 and 0.02 % of Tween™ 80 per wet weight of tannin-polysaccharide is added to the beaker and the mixture is mixed moderately for 2 hours at room temperature. The initial phase of the mixing process is done by the use of the Dispax-Reactor from Ika works (lab version) until the particles of the polysaccharide have been reduced to a very fine particle size. The mixture is then left to stand at room temperature and, after about 24 hours, two clear phases have formed. The top phase includes the clear polysaccharide, and the lower phase includes the dark brown polyethylene glycol-tannin complex. The liquids are then centrifuged at 10,000 rpm. The top layer is removed carefully, and the final liquid is lyophilized to form a dry polysaccharide.

EXAMPLE 6

This example shows another similar procedure for the disruption of the tannin-polysaccharide complex obtained according to Example 1, using a non-solvent approach. To illustrate this technique, 1 gram (wet weight) of the polysaccharide complex obtained in Example 1 is placed into a of 200 ml beaker containing a 1% weight/volume of gelatin (Bacto-Labs; Lot Number 0143–01–7) previously dissolved therein. The initial mixing process was done in a Dispax-Reactor from Ika works (lab version) until the particles of the polysaccharide had been reduced to a very fine particle size. The mixture is then left to stand at room temperature and, after about 24 hours, two clear phases had formed. The top phase included the clear polysaccharide while the lower phase included the insoluble particles. The liquids were then centrifuged at 10,000 rpm. The top layer was removed carefully, and the final liquid lyophilized to form a dry polysaccharide.

EXAMPLE 7

This example illustrates an application using a microbial fermented extract. Cultivated mycelia of Coriolus versicolor are filtered, pressed to remove any associated water, and dried under vacuum for 48 hours. One kg of the dried mycelium is pulverized into a fine powder, mixed with 15 liters of distilled water, and placed into a stainless steel reactor vessel having a nominal working volume of 30 liters. The vessel's contents are mixed while heating rapidly with an electrical heating mantle to 100 degrees Celsius for a period of 3 hours. Then the liquid is filtered, and the filtered material is allowed to cool to room temperature. The pH is adjusted to 4.5 followed by the addition of 550 niL of a 10% w/v of tannic acid with mixing for 20 minutes. The solid complex that forms is recovered and placed into an explosion proof blender along with 350 mL of acetone which containing 0.02% of Tween 80 w/w per weight of the tannic acid complex and 2.0% v/v of Carbowax™ 8000 per volume of acetone used. The particle size of the solids in the mixture is then reduced. The solvent is decanted, and a second wash is done using 110 ml of a mixture of acetone:water in a ratio of 70:30 containing 0.02% of Tween 80 w/w per weight of the tannic acid complex and 2.0% v/v of Carbowax™ 8000 per volume of acetone. Two more similar washings are done until little to no tannic acid is detected qualitatively, using ferric chloride solution, in the organic solvent or filtrate. The final solid then is dried under vacuum.

EXAMPLE 8

Lentinus edodes (Berk.) also known as Shiitake Mushroom was purchased from North American Reishi as powder material. 200 g of this material were mixed with 1000 ml of distilled water, and heated for 8 hours at 100 degrees Celsius and extracted three times. All extract pools were combined and concentrated under vacuum until a final volume of 300 mL was reached. Once the solution reached room temperature, 37 mL of a 2% solution of tannic acid was added. A milky suspension formed and, after centrifugation, the pellet was washed as described in Example 1 with a mixture of acetone and water (70:30; v/v). After all tannins were removed, a final 0.42 grams of lentinan crude polysaccharide were obtained.

EXAMPLE 9

One kilogram of defatted and stabilized oat bran having a beta glucan content of approximately 6.5% w/w was mixed for 24 hours at room temperature with 20 liters of aqueous 0.25 N of NaOH to raise the pH of the solution to about 10. Then, the liquid mixture was centrifuged to separate the soluble beta glucan solution from the remaining solids. 0.25 g of calcium chloride were added, and the pH was adjusted to 6.2. This solution was then placed into a stainless steel reactor vessel along with 0.75 mL of the alpha amylase (Validase HT 340 L) having an activity of 340,000 Modified Wohlgemuth units/ml. The solution temperature was raised rapidly to 90 degrees C and kept there for 3 minutes. The solution was allowed to cool to 60 degrees C. The pH was adjusted to 4.5, and 2.5 ml of the fungal glucoamylase enzyme (Validase GA) with an activity of 300 AG units/mL was added. The temperature and pH were kept constant for 3 hours. At the end of 3 hours, the temperature was raised rapidly to 80 degrees C, held there for 5 minutes, and then allowed to cool to room temperature. The final liquid mixture was centrifuged to remove the suspended solid material, and the remaining liquid was treated with 800 ml of a 10% w/w tannic acid solution. After mixing for about 20 minutes, an agglomerate mass formed, which was removed by conventional filtration. The filter cake was pressed against a nylon cloth to remove the associated water, and then treated with 900 ml of an acetone solution containing 2% of Carbowa™ 8000 w/volume of solvent and 0.02% of Tween™ 80 per weight of wet solid. The mixture was blended with 3 second pulsations until all the solid mass disintegrated. The supernatant was removed and the solid was washed with 250 ml of a 70:30 acetone:water mixture containing 2% of Carbowa™ 8000 w/v and 0.02% of Tween™ 80 of original wet solid. Then, 3 consecutive washes were done with 250 ml of a 70:30 acetone: water mixture in order to wash out the remaining tannins. The final solid was dried under vacuum for 24 hours.

EXAMPLE 10

0.25 g. of the final dried power of aloe polysaccharide obtained from Example 1 was mixed with 100 ml of water with the aid of an homogenizer. Once the polysaccharide was fully dispersed in solution, 97 parts of this final solution were mixed and blended with 1 part of glycereth-26 (made by Croda Oleochemicals) for 10 minutes. 1 part of Lidocaine HCL was added and this mixture was blended for an additional 10 minutes. 1 part of Germaben II (Sutton laboratories; a mixture of propylene glycol, diazolidinyl urea, methylparaben, and propylparaben) was added and the combination was blended 1 minute. This gel-like mixture was found to be an excellent anti-inflammatory ointment and has a very good texture and feel.

EXAMPLE 11

1 g of the final beta glucan mixture obtained from Example 6 is mixed with 100 ml of water, and the polysaccharide dispersed by using an homogenizer. Once the polysaccharide is fully dispersed in solution, 80.59 g of this 1% beta glucan solution is mixed with 0.2 g of methylparaben, 0.65 g of Allantoin, 0.2 g of panthenol DL, 0.7 g of glycerin UPS, 0.05 g of tetrasodium EDTA, and 0.2 g of urea UPS. This mixture makes up "Group A". In a separate beaker, 5 g of Caprylic/Capric Glyceride (Dr. Straetmans, HulsAG/Huls America), is mixed with 0.5 g of jojoba oil, 1.3 g of sunflower oil, 2.3 g of Glycereth-26 (Croda Oleochemicals), 1.8 g of cetyl alcohol, 2.9 g of stearic acid, 0.3 g of lanolin alcohol, 0.8 g of Floraesters 30 (jojoba esters made by Floratech ), 0.3 g of Myverol 18–07K (distilled monoglycerides made by Eastman chemical), 0.01 g of tocopheryl acetate, and 0.1 g of Vitamin A palmitate. This group of chemicals constitutes "Group B". For the manufacture of a good moisturizing cream, Groups A and B are both heated to 75 degrees C. and Group B is poured slowly into Group A. While this mixture is still at approximately 65 degrees C. 0.6 g of triethanolamine is added slowly to the mixture under constant mixing. Once the temperature of the final cream cools to 45 degrees C. a mixture of 1 g of Germal II 1:1 solution (diazolidinyl urea made by Sutton laboratories ) and 0.5 g of Gardenia 144548–1296A (fragrance made by Belmay Labs USA) is added. The final cream has a very good texture, viscosity, and moisturizing feel.

EXAMPLE 12

The polysaccharide prepared according to Example 1 was characterized according to molecular weight, acetyl group: saccharide molar ratio content, saccharide content, linkage group analysis, and saccharide-linkage end group content. It will be understood by the artisan of ordinary skill that different analytical tests will provide physical property values for the native polysaccharide that may or may not be different than the physical property values of the polysaccharide in the actual native state. Polysaccharides prepared according to the invention will generally possess at least one, preferably at least two, and more preferably at least three physical properties having values similar to a native polysaccharide tested using the same analytical tests and conditions. Accordingly, a polysaccharide prepared according to the invention will generally possess physical properties similar to, or approximating, those of the native polysaccharide when the physical properties are determined using the same analytical tests and conditions.

Molecular Weight Analysis

The weight average (Mw), number average (Mn) and Z-average (Mz) molecular weights as well as the dispersity (Mw/Mn) of the polysaccharide were determined by size exclusion chromatography on distribution using pullulan and poly(ethylene oxide) molecular weight standards and 2000 angstrom and 1000 angstrom cut-off size exclusion columns. The molecular weight distributions of native aloe polysaccharide (FIG. 1a) and the polysaccharide prepared according to the invention (Vitto-Mannan™; FIG. 1b) were compared. The values reported that Vito-Mannan polysaccharide (assigned as polysaccharide number 2) has an average molecular weight of 1,709,000 which is slightly lower as compared with the value of 1,855,00 of the Aloe standard and the value of 1,839,000 for the Mannopol biopolymer. However, during the perfomance of the trial some insoluble material was present in the mannopol sample, while Vito-Mannan™ and the standard were totally soluble in water. Also an important note to consider here for the interpretation of this data is the concept of Mw and Mn given by the HPLC Size exclusion analysis. The value of Mn is the simple average of the total mass of the chains divided by the number of chains. The weight average molecular weight Mw is the summation of the square of the molecular weights divided by the summation of the molecular weights of all molecules present. Since Mw is always greater than Mn, then the narrower the distribution, the closer Mn and Mw are. The ratio of Mw/Mn and is referred to as the dispersivity value. As the distribution narrows, then the dispersivity approaches the value of 1 and such a polymer is referred to as mono disperse. Alternatively as the value of Mw/Mn increases above 1, it is referred to as poly-disperse. Aloe polysaccharide is a poly-disperse acetylated mannan. The molecular weight distribution of Vito-mannan™ product resembles that of the native aloe polysaccharide more than does that of the Mannapol™ product. The dispersity value of Mw/Mn for Vito-Mannan is 2.18 as compared to 2.71 of the standard and obviously higher than for the case of Mannopol which is 1.79.

Figure 1C:
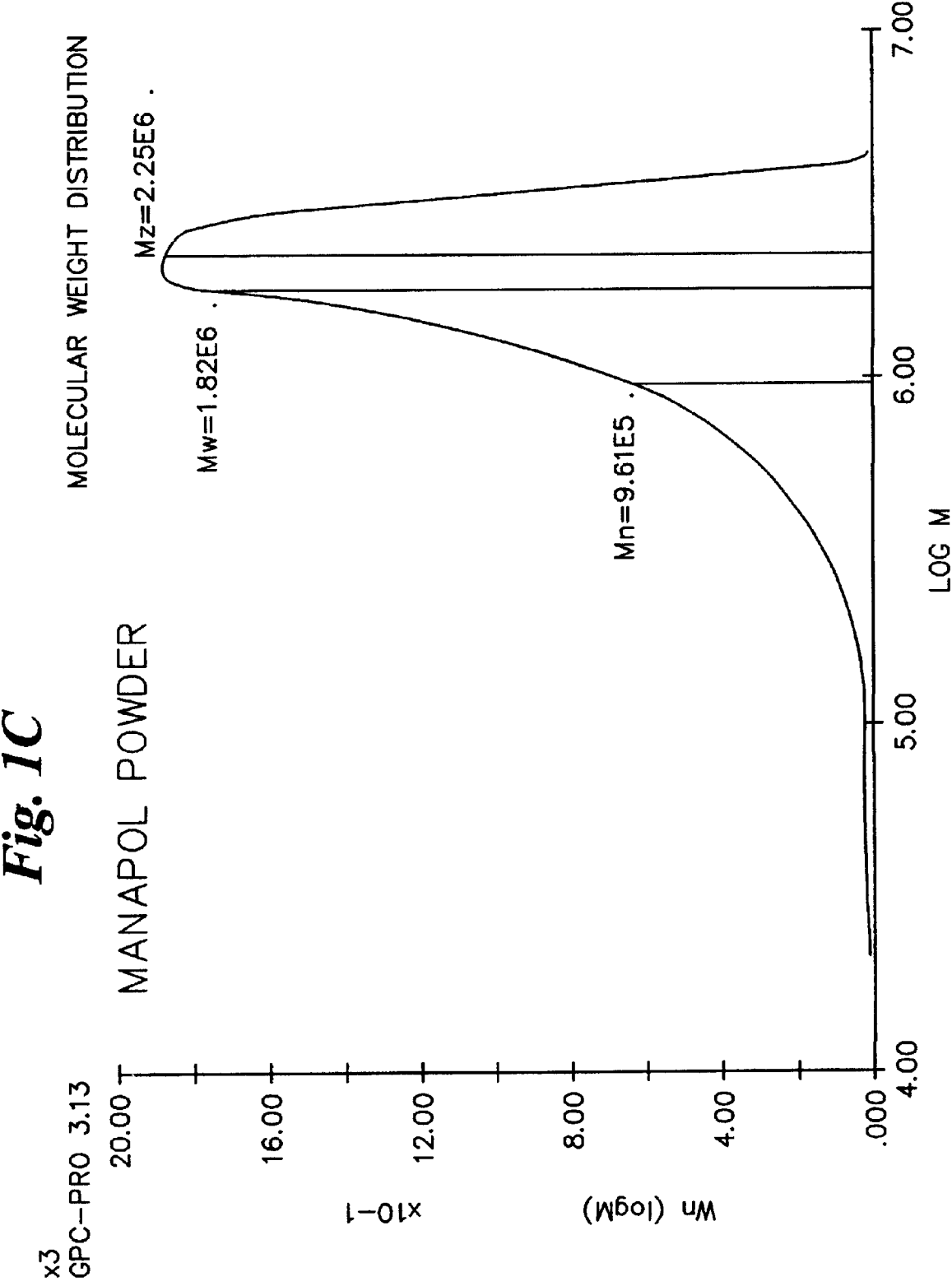

The polysaccharides which chromatograms are depicted in FIGS. 1a–1c are generally characterized by the following molecular weight parameters.

| Parameter | Native Aloe | Vito-Mannan ™ (Invention) | Mannapol ™ (Prior Art) |
|---|---|---|---|
| $M_w$ | 1,855,000 | 1,709,000 | 1,839,000 |
| $M_n$ | 683,900 | 783,700 | 1,025,000 |
| $M_z$ | 2,367,000 | 2,216,000 | 2,249,000 |
| $M_w/M_n$ | 2.71 | 2.18 | 1.79 |
| Amount w/$M_w$ > 1,000,000 | 75.8% | 71.2% | 79.7% |
| Amount w/5000,000 ≦ $M_w$ ≦ 1,000,000 | 13.2% | 16.7% | 13.2% |
| Amount w/$M_w$ < 500,000 | 11.0% | 12.1% | 7.1% |

Acetyl Grou: Saccharide Ratio Content

The molar ratio of acetyl groups: per saccharide residues in native aloe polysaccharide was compared to that of Vitto-Mannan™ and Mannapol™ using a proton NMR based method wherein the signals assigned to acetyl group protons and mannose residue protons were integrated and their molar adjusted values compared. The ratio for acetyl groups: saccharide residues and the percentage of acetyl groups present in the aloe polysaccharide are shown in the table as follows:

| Parameter | Native | Vitto-Mannan ™ | Mannapol ™ |
|---|---|---|---|
| Acetyl group/total saccharide | 0.936–0.96 | 0.87–0.956 | 0.455–0.575 |
| Acetyl group/ mannose saccharide | 1.04–1.1 | 0.971–1.201 | 0.466–0.491 |

The ratio of acetyl groups: total saccharides for Vitto-Mannan™ closely approximates that of the native aloe polysaccharide and can range from about 0.85 to about 0.96.

Acetyl Group Content

The $^1$H NMR analyses were done using a 400 MHz NMR instrument. Experimental conditions were as follows: About 5–10 mg of aloe polysaccharide was placed in a 5 mm NMR tube. We added 0.2% w/w DC1 in $D_2$O to the proper volume and slightly heated the suspension until the material dissolved completely. Note that if $D_2$O is used alone, the aloe polysaccharide does not form a true solution, but rather a rigid gel. This lead into a non homogeneous magnetic field over the sample volume, effectively widening the water resonance and causing the polysaccharide resonances to broaden considerably. By adding 0.2% DC1 w/w in $D_2O$, it will cause only slight hydrolyses of glycosidic linkages and acetate esters, and a more ideal solution is eventually formed. The carbohydrate signals as well as the water resonance become sharper. All the runs were done at a temperature of 85 degrees Celsius, 8.0 sec presaturation of the water signal at 4.3 ppm, 90 pulse, acquisition time of 3.7 sec, 16 to 32 transients. For the calculations of the acetyl: saccharide ratio, 7 protons are assumed per saccharide and 3 for the case of the methyl group of the acetyl. For the case of the determination of the percentage of acetyl groups present in the Aloe polysaccharide samples, the values are reported as percentage of acetic acid. A sample calculation as for the case of the 22% found in the Vitto-Mannan™ one goes as follows:

100×NMR area of acetic acid/NMR area of maleic acid× ⅔× molecular weight of acetic acid (60)/Molecular weight of Maleic acid (116)×weight of maleic acid added to the sample (7,08)/weight of the sample (17.3)=22%. In theory, we have found that the ratio of the molecular weight of acetic acid (60)/molecular weight of saccharide (Considered Mannose minus 18 of $H_2O$ is 162 gives a value of 0.37. If we convert it to weight percentage then 0.37/1.37×100=27% is the theoretical value for the native aloe. For Vito-mannan the experimental value was 21.96%.

The theoretical value for the amount of acetylation of native aloe polysaccharides is about 27% assuming that all of the polysaccharides present in the native product are mannose residues. The experimental values obtained for the native, Vitto-Mannan™ and Mannapol™ products were as follows:

| Parameter | Native | Vitto-Mannan ™ | Mannapol ™ |
| --- | --- | --- | --- |
| Total acetyl group content (%) | 19.95 | 19.7–21.96 | 4.96 |

Accordingly, the product of the present invention has an acetyl group content closely approximating that of the native aloe polysaccharide. The differences between the experimental and theoretical values for the native product explain why the Vitto-Mannan™ product yielded values that were less than theoretical.

Saccharide Content:

The saccharide contents of native aloe polysaccharide, Vitto-Mannan™ and Mannapol™ were compared by gas chromatographic analysis of the acid degraded and Tri-Sil derivatized polysaccharides using myo-inositol as an internal standard. The polysaccharides contained the following saccharides, wherein the amounts indicate the percent by weight based upon the dry weigh of the polysaccharide.

| Saccharide | Native Polysaccharide | Vitto-Mannan ™ | Mannanol ™ |
| --- | --- | --- | --- |
| Arabinose | 1.1 | 0.9 | 2.4 |
| Rhamnose | 0.3 | 0.1 | 1.8 |
| Xylose | 0.4 | 0.4 | 8.6 |
| Mannose | 81.0 | 83.1 | 31.5 |
| Glucose | 17.2 | 15.5 | 12.3 |
| Fucose | | | 1.1 |
| Galactose | | | 10.2 |
| Galacturonic Acid | | | 32.1 |

Accordingly, the Vito-Mannan™ polysaccharide has a saccharide content that is substantially similar to that of native aloe polysaccharide. The Mannapol™ polysaccharide, however, has a saccharide content that is not at all similar to native aloe polysaccharide and is, in fact, highly contaminated with significant amounts of galactose and galacturonic acid which are found in the skin of the aloe leaf.

End Group Content and Linkage Group Analysis

The end group content and linkage group analyses were determined by gas chromatography using the method of Ciucanu and Kerek (Carbohydr. Res. (1984), 131,: 209–217). The polysaccharides were methylated with NaOH and methyl iodide and subsequently hydrolyzed with trifluoroacetic acid, reduced with sodium borodeuteride, and acetylated with acetic anhydride. The samples were then analyzed on a Supelco™ Sp2330 column using derivatized myo-inositol as an internal standard. The results below indicate the percent by weight content of each saccharide with respect to the dry weight of the respective polysaccharide.

| Saccharide | Native Polysaccharide | Vitto-Mannan ™ | Mannapol ™ |
| --- | --- | --- | --- |
| Terminal arabinose (furanose) | 0.8 | 0.7 | 0.9 |
| Terminal xylose | — | — | 0.7 |
| Terminal mannose | 1.1 | 0.9 | 0.5 |
| Terminal galactose | 0.4 | 0.5 | 1.0 |
| 4-xylose | 0.7 | 0.7 | 2.4 |
| 4-mannose | 68.3 | 69.6 | 67.0 |
| 4-glucose | 10.0 | 9.7 | 18.4 |
| 3,4-mannose | 4.1 | 4.0 | 1.5 |
| 2,4-mannose | 2.9 | 2.5 | 0.9 |
| 2,3,6-mannose | 2.1 | 2.3 | 1.2 |
| 4,6-mannose | 5.3 | 5.4 | 1.6 |
| 4,6-glucose | 0.5 | 0.5 | 2.0 |
| 3,6-galactose | 1.4 | 1.4 | 1.9 |
| 3,4,6-mannose | 0.9 | 0.8 | — |
| 2,4,6-mannose | 0.9 | 0.8 | — |
| 2,3,4,6-mannose | 0.6 | 0.7 | — |

Accordingly, the Vito-mannan™ polysaccharide is very similar to the native polysaccharide; however, the Mannapol™ polysaccharide is very different than the native polysaccharide.

Linkage analysis

All the three samples were methylated using the NaOH/Me method. (I.Ciucanu and F.Kerek. 1984. Carbohydr. Res., 131:209–217.), then methylated in 2 M TFA at 121 degrees celcius for 2 hours and the hydrolyzed carbohydrate was reduced with sodium borodeuteride at room temperature. The product was acetylated using acetic anhydride at 120 degrees celcius for 3 hours. The derivatized samples were analyzed by GC-MS using Sp2330 Supelco™ column. The internal standard myo-inositol was added to each sample prior to the reduction step.

Composition Analysis

All the three samples were separately ground to a powder in a pestle and mortar. The samples were then hydrolyzed using freshly prepared 1 M methanolic-HCl for 16 hours at 80 degrees centigrade. The released sugars were derivatized with the use of Tri-Sil and the samples were run on a GC using a Supelco column. Myo-inositol was also added (20 micrograms) as an internal standard. Sample number three known as Mannapol™ was slightly insoluble in the methanolic/HCl solution. Whereas samples coded as Aloe polysaccharide and Vitto-Mannan™ were insoluble in the methanolic/HCl.

EXAMPLE 13

An aloe polysaccharide-containing beverage comprising the Vito-mannan™ polysaccharide was prepared as follows.

For the preparation of a 1 L beverage, 2.0 g of Vito-mannan™ were dissolved and rehydrated in 600 ml of water with a homogenizer and sterilized with 30 Krad of gamma radiation. 60 g of fructose was then added followed by 1 g of magnesium carbonate in 50 ml, 2.5 g of potassium citrate in 50 ml of water, vitamin E in 100 ml of water, and vitamin C in 100 ml of water. The mixture was then pasteurized and upon cooling 1 g of potassium sorbate in 50 ml of water was added. The pH was adjusted to 3.5 with a 1 g mixture of citric acid and malic acid. 3.5 g of a natural flavor was finally added. The drink had an acceptable shelf-life and good taste. The drink is substantially free of anthraquinones and is pulp free. The presence of 0.2% w/v of Vitto-Mannan™ polysaccharide in the beverage provides the user the same approximate concentration of native polysaccharide as is present in the aloe vera leaf.

A beverage prepared according to the above procedure has the following general formulation:

| Ingredient | Content (w/v) |
|---|---|
| Vito-Mannan ™ | 0.2 |
| Natural fruit flavor (blend of papaya, orange and lemon) | 0.25 |
| Tocophery Acetate (vitamin E) | 0.1 |
| Ascorbyl palmitate complex (vitamin C) | 0.1 |
| Citric acid and malic acid mixture | 0.1 to pH 3.5 |
| Magnesium carbonate | 0.1 |
| Fructose (inulin HD-oligosaccharide) | 6 |
| Potassium Citrate | 0.25 |
| USP potassium sorbate | 0.1 |
| USP sodium benzoate | 0.1 |
| Water | Remainder to 100% |

The above is a detailed description of particular embodiments of the invention. Those of skill in the art should, in light of the present disclosure, appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

What is claimed is:

1. A method of isolating a mucilaginous polysaccharide, the method comprising:
    a) contacting a tannin and an aqueous preparation comprising the polysaccharide at a pH not greater than about 7.0 to form a substantially insoluble complex comprising the polysaccharide; and
    b) thereafter separating the complex and the remainder of the preparation.
2. The method of claim 1, wherein the preparation is obtained from a plant.
3. The method of claim 2, wherein the plant is a plant of a genus selected from the group consisting of Aloe, Plantago, Cassia, and Sorghum.
4. The method of claim 3, wherein the plant is a plant of the genus Aloe.
5. The method of claim 4, wherein the plant is Aloe vera.
6. The method of claim 4, wherein the plant is Aloe barbadensis miller.
7. The method of claim 3, wherein the plant is a plant of the genus Plantago.
8. The method of claim 7, wherein the plant is selected from the group consisting of Plantago ovata and Plantago major.
9. The method of claim 3, wherein the plant is Cassia augustifolia.
10. The method of claim 3, wherein the plant is Sorghum bicolor.
11. The method of claim 2 wherein the plant is a cereal plant.
12. The method of claim 11, wherein the plant is an oat.
13. The method of claim 1, wherein the preparation is obtained from a fungus.
14. The method of claim 13, wherein the fungus is a fungus of a genus selected from the group consisting of Criolus, Lentinula, Grifola, and Ganoderma.
15. The method of claim 14, wherein the fungus is selected from the group consisting of Criolus versicolor, Lentinula edodes, Grifola frondosa, and Ganoderma lucidum.
16. The method of claim 1, wherein the preparation is obtained from a cultured microorganism.
17. The method of claim 1, wherein the tannin is selected from the group consisting of hydrolyzable tannins and condensed tannins.
18. The method of claim 17, wherein the tannin is a hydrolyzable tannin.
19. The method of claim 18, wherein the tannin is selected from the group consisting of gallotannins and ellagitannins.
20. The method of claim 19, wherein the tannin is selected from the group consisting of Chinese gallotannin, Turkish gallotanin, tara gallotannin, myrobalan ellagitannin, divi divi ellagitannin, and chestnut ellagitannin.
21. The method of claim 1, wherein the tannin is selected from the group consisting of nobotanin, corilagin, gemin, augosin, rugosin, isorugosin, corousilin, coriarium, ocnothein, agrimonin, geraniin, granatin and cornusiin.
22. The method of claim 1, wherein the tannin is added in an amount from 1 to 100 milligrams per milliliter of the preparation.
23. The method of claim 22, wherein the tannin is a ellagitannin and is added in an amount from 1 to 5 milligrams per milliliter of the preparation.
24. The method of claim 22, wherein the tannin is a gallotannin and is added in an amount from 5 to 100 milligrams per milliliter of the preparation.
25. The method of claim 1, wherein the tannin and the preparation are contacted at a pH not greater than about 5.5.
26. The method of claim 25, wherein the tannin and the preparation are contacted at a pH in the range from 3 to 5.
27. The method of claim 26, wherein the tannin and the preparation are contacted at a pH of about 4.5.
28. The method of claim 1, wherein the complex comprises a polysaccharide selected from the group consisting of a 1–3, 1–4 beta glucan; an acetylated polymannan; a mucilage wherein the main chain comprises beta 1–4 acetylated D-xylopyranose residues; a galactomannan; and a protein-bound, water soluble 1–3 beta-D-glucan.
29. The method of claim 1, wherein the preparation is obtained from Aloe vera and wherein the polysaccharide in the complex comprises:
    arabinose residues in the range of about 0.8–1.2% by weight;
    rhamnose residues in the range of about 0.08–0.35% by weight;
    xylose residues in the range of about 0.35–0.45% by weight;
    mannose residues in the range of about 80–85% by weight; and glucose residues in the range of about 14–18% by weight; based upon the dry weight of the polysaccharide.

30. The method of claim 29, wherein the molar ratio of (acetyl moieties/total saccharide residues) is from 0.87 to 0.965 and wherein the molar ratio of (acetyl moieties/ mannose residues) is from 0.971 to 1.201 for the polysaccharide in the complex.

31. The method of claim 1, further comprising
  c) thereafter combining the complex and an aqueous solution to form a product.

32. The method of claim 31, wherein the complex is substantially dried prior to combining it with the aqueous solution.

33. The method of claim 31, wherein the complex is combined with an amount of the aqueous solution such that the final concentration of the polysaccharide in the product is from 0.2% to 0.6% (w/v).

34. The method of claim 1, further comprising removing at least a portion of the tannin from the complex by:
  c) thereafter contacting the complex and a wash solution; and
  d) thereafter separating the complex and the wash solution.

35. The method of claim 34, wherein each of c) and d) is repeated multiple times.

36. The method of claim 34, wherein substantially all of the tannin is removed from the complex.

37. The method of claim 34, wherein the wash solution comprises an ingredient selected from the group consisting of an organic solvent, a surfactant, a glycol polymer, a soluble poly(vinylpyrrolidone), an insoluble poly (vinylpyrrolidone), a protein, an animal hide powder, a powdered nylon, a polystyrene, a polyacrylate, a phenol specific resin, a cation exchange resin, an anion exchange resin, a surfactant, and water.

38. The method of claim 37, wherein the wash solution comprises an organic solvent selected from the group consisting of methanol, ethanol, acetone, butanol, and 1,3 dioxalane.

39. The method of claim 37, wherein the ingredient is a protein selected from the group consisting of gelatin and casein.

40. The method of claim 37, wherein the wash solution comprises water and an ingredient selected from the group consisting of an organic solvent, a surfactant, a glycol polymer, and a protein.

41. The method of claim 40, wherein the wash solution comprises acetone.

42. The method of claim 41, wherein the wash solution comprises a polyethylene glycol and a surfactant.

43. The method of claim 34, wherein the particle size of the complex is reduced prior to separating the complex and the wash solution.

44. The method of claim 34, further comprising
  e) thereafter combining the complex and an aqueous solution to form a product.

45. The method of claim 44, wherein the complex is substantially dried prior to combining it with the aqueous solution.

46. The method of claim 44, wherein the complex is combined with an amount of the aqueous solution such that the final concentration of the polysaccharide in the product is from 0.2% to 0.6% (w/v).

47. The method of claim 44, further comprising incorporating a preservative in the product.

48. The method of claim 44, wherein the particle size of the complex is reduced prior to combining the complex and the aqueous solution.

49. The method of claim 44, wherein the color of the complex is reduced prior to combining the complex and the aqueous solution.

50. The method of claim 44, wherein the product is selected from the group consisting of a beverage, a candy, a comestible, a tonic, a lotion, a cosmetic, a pharmaceutical composition, a suppository, an implant, a shampoo, a hair conditioner, a wound dressing, a wound or injury treatment product, an anti-itch formulation, a sun-burn formulation, a dietary composition, and a food supplement.

51. The method of claim 44, wherein the product is formulated for administration to a human by a route selected from the group consisting of an oral route, a topical route, and an injectable route.

* * * * *

UNITED STATES PATENT AND TRADEMARK OFFICE
CERTIFICATE OF CORRECTION

PATENT NO. : 6,482,942 B1
DATED : November 19, 2002
INVENTOR(S) : Natale Vittori It is certified that error appears in the above-identified patent and that said Letters Patent is hereby corrected as shown below:

Column 7,
Line 38, "MANNAPOL" should read -- Manapol --

Column 17,
Lines 57 and 64, "Vito-Mannan" should read -- Vitto-Mannan --
Line 61, "Mannopol" should read -- Manapol --
Line 63, "mannopol" should read -- Manapol --

Column 18,
Line 13, "Vito-mannan" should read -- Vitto-Mannan --
Lines 15, 38 and 48, "Mannapol" should read -- Manapol --
Line 16, "Vito-Mannan" should read -- Vitto-Mannan --
Line 15, "Mannopol" should read -- Manapol --
Line 24, in the Table, "Vito-Mannan" should read -- Vitto-Mannan --
Line 24, in the Table, "Mannopol" should read -- Manapol --

Column 19,
Lines 23 and 65, "Vito-mannan" should read -- Vitto-Mannan --
Lines 29, 34, 47 and 67, "Mannopol" should read -- Manapol --
Line 55, "Mannanol" should read -- Manapol --

Column 20,
Lines 38 and 67, "Vito-mannan" should read -- Vitto-Mannan --
Lines 39-40 and 60, "Mannapol" should read -- Manapol --
Line 62, "Vito-Mannan" should read -- Vitto-Mannan --

UNITED STATES PATENT AND TRADEMARK OFFICE
CERTIFICATE OF CORRECTION

PATENT NO.   : 6,482,942 B1
DATED         : November 19, 2002
INVENTOR(S)  : Natale Vittori It is certified that error appears in the above-identified patent and that said Letters Patent is hereby corrected as shown below:

<u>Column 21,</u>
Lines 1 and 2, "Vito-mannan" should read -- Vitto-Mannan --
Line 23, in the table, "Vito-Mannan" should read -- Vitto-Mannan --

Signed and Sealed this

Sixth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,482,942 B1
DATED : November 19, 2002
INVENTOR(S) : Natale Vittori It is certified that error appears in the above-identified patent and that said Letters Patent is hereby corrected as shown below:

Column 7,
Line 38, "MANNAPOL" should read -- Manapol --

Column 17,
Lines 57 and 64, "Vito-Mannan" should read -- Vitto-Mannan --
Line 61, "Mannopol" should read -- Manapol --
Line 63, "mannopol" should read -- Manapol --

Column 18,
Line 13, "Vito-mannan" should read -- Vitto-Mannan --
Lines 15, 18, 38 and 48, "Mannapol" should read -- Manapol --
Line 16, "Vito-Mannan" should read -- Vitto-Mannan --
Line 15, "Mannopol" should read -- Manapol --
Line 24, in the Table, "Vito-Mannan" should read -- Vitto-Mannan --
Line 24, in the Table, "Mannopol" should read -- Manapol --

Column 19,
Lines 23 and 65, "Vito-mannan" should read -- Vitto-Mannan --
Lines 29, 34, 47 and 67, "Mannopol" should read -- Manapol --
Line 55, "Mannanol" should read -- Manapol --

Column 20,
Lines 38 and 67, "Vito-mannan" should read -- Vitto-Mannan --
Lines 39-40 and 60, "Mannapol" should read -- Manapol --
Line 62, "Vito-Mannan" should read -- Vitto-Mannan --

UNITED STATES PATENT AND TRADEMARK OFFICE
CERTIFICATE OF CORRECTION

PATENT NO. : 6,482,942 B1
DATED : November 19, 2002
INVENTOR(S) : Natale Vittori It is certified that error appears in the above-identified patent and that said Letters Patent is hereby corrected as shown below:

Column 21,
Lines 1 and 2, "Vito-mannan" should read -- Vitto-Mannan --
Line 23, in the table, "Vito-Mannan" should read -- Vitto-Mannan --

This certificate supersedes Certificate of Correction issued May 6, 2003.

Signed and Sealed this

Fifth Day of August, 2003

JAMES E. ROGAN
*Director of the United States Patent and Trademark Office*